United States Patent [19]

Schaus

[11] Patent Number: 4,537,964
[45] Date of Patent: * Aug. 27, 1985

[54] METHOD OF PREPARING PERMISSIBLY-SUBSTITUTED 1H(AND 2H)PYRAZOLO[3,4-G]QUINOLINES; PYRIMIDO[4,5,G]QUINOLINES; THIAZOLO[4,5,G]QUINOLINES AND INTERMEDIATES THEREFORE

[75] Inventor: John M. Schaus, Indianapolis, Ind.

[73] Assignee: Eli Lilly and Company, Indianapolis, Ind.

[*] Notice: The portion of the term of this patent subsequent to Aug. 27, 2002 has been disclaimed.

[21] Appl. No.: 637,665

[22] Filed: Aug. 3, 1984

[51] Int. Cl.$^3$ .................. C07D 255/04; C07D 273/01; C07D 285/00
[52] U.S. Cl. ...................... 544/250; 546/82; 546/83; 546/84; 546/134; 546/153; 546/157; 546/119; 546/15; 549/341; 560/125; 560/115; 562/507
[58] Field of Search ...................... 546/82, 84, 83, 134, 546/153, 157, 119, 15; 424/258; 544/250; 549/341; 560/125, 115; 562/507

[56] References Cited

U.S. PATENT DOCUMENTS 4,198,415 4/1980 Kornfeld et al. .................. 424/258

OTHER PUBLICATIONS

March, *Advanced Organic Chemistry* 2nd Ed., McGraw-Hill (1977) pp. 346–347; 484–485; 710–711.
March, *Advanced Organic Chemistry*, 1st Ed., McGraw-Hill (1968), p. 337.
Buehler and Pearson, *Survey of Organic Synthesis*, 1970, pp. 2,3,4,5.
Bach et al., *J. Med. Chem.*, 23, 481 (1980).
Johnson et al., *J. Org. Chem.*, 33, 3207 (1968).
Momose et al., *Chem. Pharm. Bull.*, 25, 1436 (1977) (Momose I).
Momose et al., ibid, 1797 (Monmose II).
Momose et al., ibid, 26, 620 (1978) (Momose III).

*Primary Examiner*—Henry R. Jiles
*Assistant Examiner*—P. Ann Bucci
*Attorney, Agent, or Firm*—James L. Rowe; Arthur R. Whale

[57] ABSTRACT

Trans-(±)-1-permissibly-substituted-2,6-dioxodecahydroquinoline or enantiomers thereof, intermediates for preparing tautomeric trans-(±)-5-permissibly substituted octahydro-1H(and 2H)pyrazolo[3,4-g]quinolines, 4aR,8aR or 4aS,8aS enantiomers thereof, for preparing trans-(±)-5-permissibly substituted-octahydropyrazolo (or oxazolo)[4,5-g]quinoline, 4aR,8aR or 4aS,8aS enantiomers thereof or for preparing trans-(±)-6-permissibly-substituted octahydropyrimido[4,5-g]quinolines, a 5aR,9aR or 5aS,9aS enantiomer thereof said racemic intermediates being comprised of stereoisomers of the following formulas

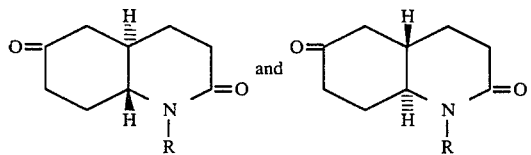

wherein R is H, alkyl or C$_{1-3}$ straight-chain alkyl.

29 Claims, No Drawings

METHOD OF PREPARING PERMISSIBLY-SUBSTITUTED 1H(AND 2H)PYRAZOLO[3,4-G]QUINOLINES; PYRIMIDO[4,5,G]QUINOLINES; THIAZOLO[4,5,G]QUINOLINES AND INTERMEDIATES THEREFORE

BACKGROUND OF THE INVENTION

Kornfeld and Bach, U.S. Pat. No. 4,198,415 disclose and claim a group of trans-($\pm$)-5-permissibly-substituted-octahydro-1H(and 2H)-pyrazolo[3,4-g]quinolines of the formulas:

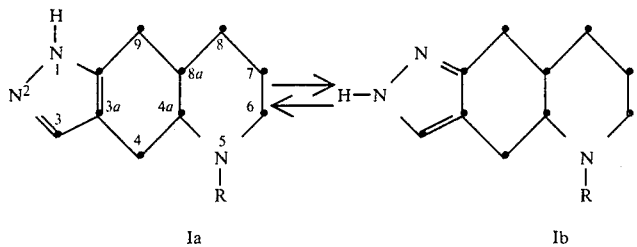

Ia                Ib wherein R is $C_{1-3}$ straight-chain alkyl. The tautomeric mixture represented by Ia and Ib above can be prepared according to Kornfeld and Bach from a trans-($\pm$)-1-$C_{1-3}$ straight-chain alkyl (or other substituent)-6-oxodecahydroquinoline (II)

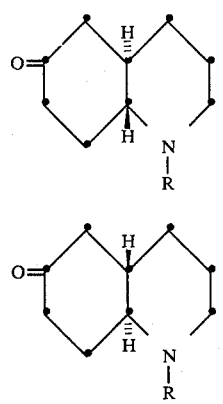

II

IIa

IIb by reaction with dimethylformamide dimethylacetal or tris(dimethylamino)methane to give the corresponding 7-dimethylaminomethylene derivative which cyclizes with hydrazine to yield the desired trans-($\pm$)-5-substituted-4,4a,5,6,7,8,8a,9-octahydro 1H(and 2H)-pyrazolo[3,4-g]quinoline. The compounds thus prepared are active as dopamine D-2 agonists, useful in treating Parkinson's Syndrome or diseases characterized by an excess of circulating prolactin. The above chemistry is amplified in Bach et al, *J. Med. Chem.*, 23, 481 (1980).

While the above chemistry has concerned the synthesis of a racemic or trans-($\pm$) tautomers, it should be apparent that the same procedures can be applied to the synthesis of the individual enantiomers, the 4aR,8aR and 4aS,8aS enantiomers. In this instance, one enantiomeric ketone, for example, the 4aR,8aR-1-substituted-6-oxodecahydroquinoline (IIa), is reacted with dimethylaminoformamide dimethylacetal and this derivative cyclized with hydrazine to yield the tautomeric pair, when R is n-propyl, 4aR,8aR-5-n-propyl-4,4a,5,6,7,8,8a,9-1H(and 2H)-octahydropyrazolo[3,4-g]quinoline (III and IIIb).

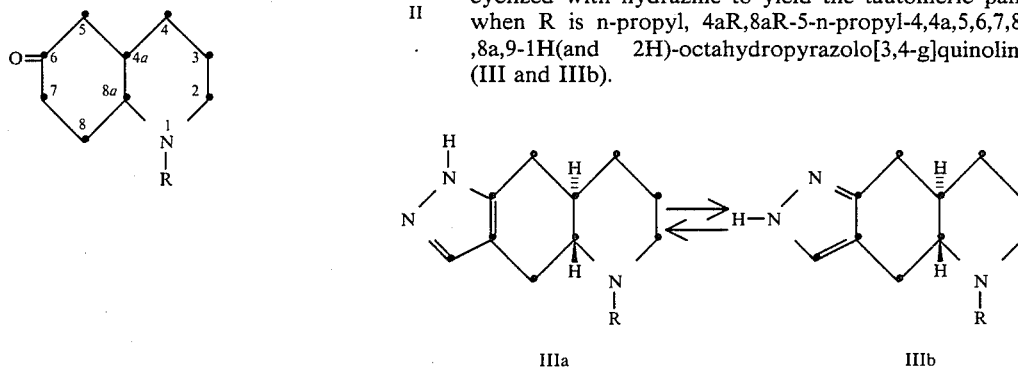

IIIa                IIIb

This compound has recently been found by Hahn et al *J.P.E.T.*, 224, 206 (1982)—see also the copending application of Hahn Ser. No. 438,833 filed Nov. 3, 1982, now U.S. Pat. No. 4,468,401, issued Aug. 28, 1984,—to be a potent antihypertensive agent. It has been given the generic name quinpirole and is currently on clinical trial in humans for the treatment of hypertension.

Quinpirole has also been found useful in the treatment of sexual dysfunction—see the copending application of Foreman, Ser. No. 518,906 filed Aug. 1, 1983. The other enantiomers, the 4aS,8aS compounds (IIIc and IIId) have been found to be dopamine D-1 agonists—see the copending application of Wong and Foreman, Ser. No. 575,126 filed Jan. 30, 1984.

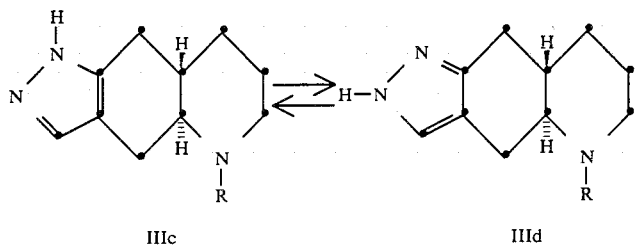

IIIc  IIId

The bicyclic ketone II is used as a starting material for the preparation of Ia and Ib. The racemate (II) is composed of two enantiomers, the 4aR,8aR and 4aS,8aS compounds (IIa and IIb). It should be noted at this point that, although the same 4aR,8aR nomenclature is used to describe the stereochemistry of both the 1-substituted-6-oxodeacahydroquinoline starting material and the 5-substituted-octahydro-1H(and 2H)-pyrazolo[3,4-g]quinoline final product, the 4a bridgehead carbon in the decahydroquinoline is the 8a carbon in the octahydro-1H(and 2H)-pyrazolo[3,4-g]quinoline final product and vice-versa. The racemic ketone (II) can be resolved into its respective enantiomers IIa and IIb by the method of Schaus and Booher, Ser. No. 439,107 filed Nov. 3, 1982, now copending. Application of the above masked formylation and hydrazine cyclization procedures to the resolved starting materials IIa or IIb yields the optically-active drugs, IIIa and IIIb or IIIc and IIId, respectively.

The racemic 1-substituted-6-oxodecahydroquinoline (II) was prepared by Kornfeld, Bach and coworkers (loc. cit.) by reacting a 4-acyloxycyclohexanone with pyrrolidine in the presence of acid to yield a pyrrolidine eneamine. Reaction of the eneamine with acrylamide gave a trans-($\pm$)-2-oxo-6-acyloxydecahydroquinoline. This derivative is then alkylated on the quinoline ring nitrogen with a $C_{1-3}$ straight-chain alkyl (or allyl) halide in the presence of sodium hydride or the like base. This 1-alkyl or allyl derivative is next treated with $LiAlH_4$ to reduce the 2-oxo group to a $CH_2$ group and simultaneously remove, by reduction, the 6-acyl group, thus producing a 1-alkyl or allyl-6-hydroxy-1,2,3,4,5,6,7,8-octahydroquinoline. Reduction with sodium cyanoborohydride and acid yielded a trans-($\pm$)-1-alkyl or allyl-6-hydroxydecahydroquinoline. Oxidation of the secondary alcohol at C-6 with chromium oxide or the like yields the racemic starting material II.

Schaus, in his copending application, Ser. No. 821,863 filed Aug. 16, 1983, provides an alternate synthetic route to II. This route involves catalytic reduction of a quaternized 6-alkoxyquinoline (quaternized with a $C_{1-3}$ straight-chain alkyl halide—an allyl halide cannot be used here because the allyl group would not survive the subsequent hydrogenation step). The product of this reaction, an 1-$C_{1-3}$ straight-chain alkyl-6-alkoxy-1,2,3,4-tetrahydroquinoline is next subjected to a Birch reduction (Li in liquid ammonia) to give a mixture of 1-$C_{1-3}$ straight-chain alkyl-6-alkoxy-1,2,3,4,5,8-hexahydroquinoline and 1-$C_{1-3}$ straight-chain alkyl-6-alkoxy-1,2,3,4,4a,5-hexahydroquinoline. Reduction of the hexahydro dreivative with sodium cyanoborohydride or the like yields an octahydro compound having a trans-fused 4a,8a ring junction. Treatment of this compound with acid hydrolyzes the 6-enol ether to produce the desired trans-($\pm$)-1-$C_{1-3}$ straight-chain alkyl-6-oxodecahydroquinoline (II).

Johnson et al, *J.Org.Chem.*, 33, 3207 (1968) describe a group of enantiomeric 1-benzyl (or unsubstituted)-6-oxo or hydroxydecahydroquinolines. The oxygenation at C-6 was accomplished by a micro-organism, using decahydroquinoline or N-benzoyl decahydroquinoline as the substrate. The micro-organism hydroxylated the substrate at C-5, C-6, or C-7. Reduction of the benzoyl group to benzyl, hydrogenolysis of the benzyl group or oxidation of the hydroxyl to a ketone were steps carried out by standard chemical procedures on the mold metabolic products. Similar microbiological transformations were carried out using the separated enantiomers as substrates. The micro-organism was quite selective as regards which of the various stereoisomers it would oxygenate.

Momose and coworkers at Osaka University have published extensively on the hydrogenation of 7-hydroxyquinoline. In Paper I appearing in *Chem.Pharm Bull.*, 25, 1436 (1977), all four stereoisomers of the trans-fused 7-hydroxydecahydroquinoline were isolated and characterized. Paper II, ibid, 1797, disclosed the synthesis of the cis-($\pm$)-7-oxodecahydroquinolines. One synthetic route involves the formation of a 2,7-dioxodecahydroquinoline in which the ketone group at C-7 was protected by ketal formation during $LiAlH_4$ reduction at C-2. In none of these cis-($\pm$) derivatives was the ring nitrogen substituted. This omission was remedied in Paper III ibid, 26, 620(1976). This paper describes the isomerization of cis-($\pm$)-1-benzyl or benzoyl-2,7-dioxodecahydroquinolines to the corresponding trans configuration.

Neither trans-($\pm$)-1-$C_{1-3}$ straight-chain alkyl or allyl-2,6-dioxodecahydroquinolines nor enantiomers thereof have been described.

DESCRIPTION OF THE INVENTION

This invention provides a method of preparing trans-($\pm$)-1-optionally-substituted-4,4a,5,6,7,8,8a,9-octahydro-1H(and 2H)-pyrazolo[3,4-g]quinolines of Formula I, or an enantiomers thereof, (IIIa and IIIb) according to the procedure set forth in Synthetic Route I below

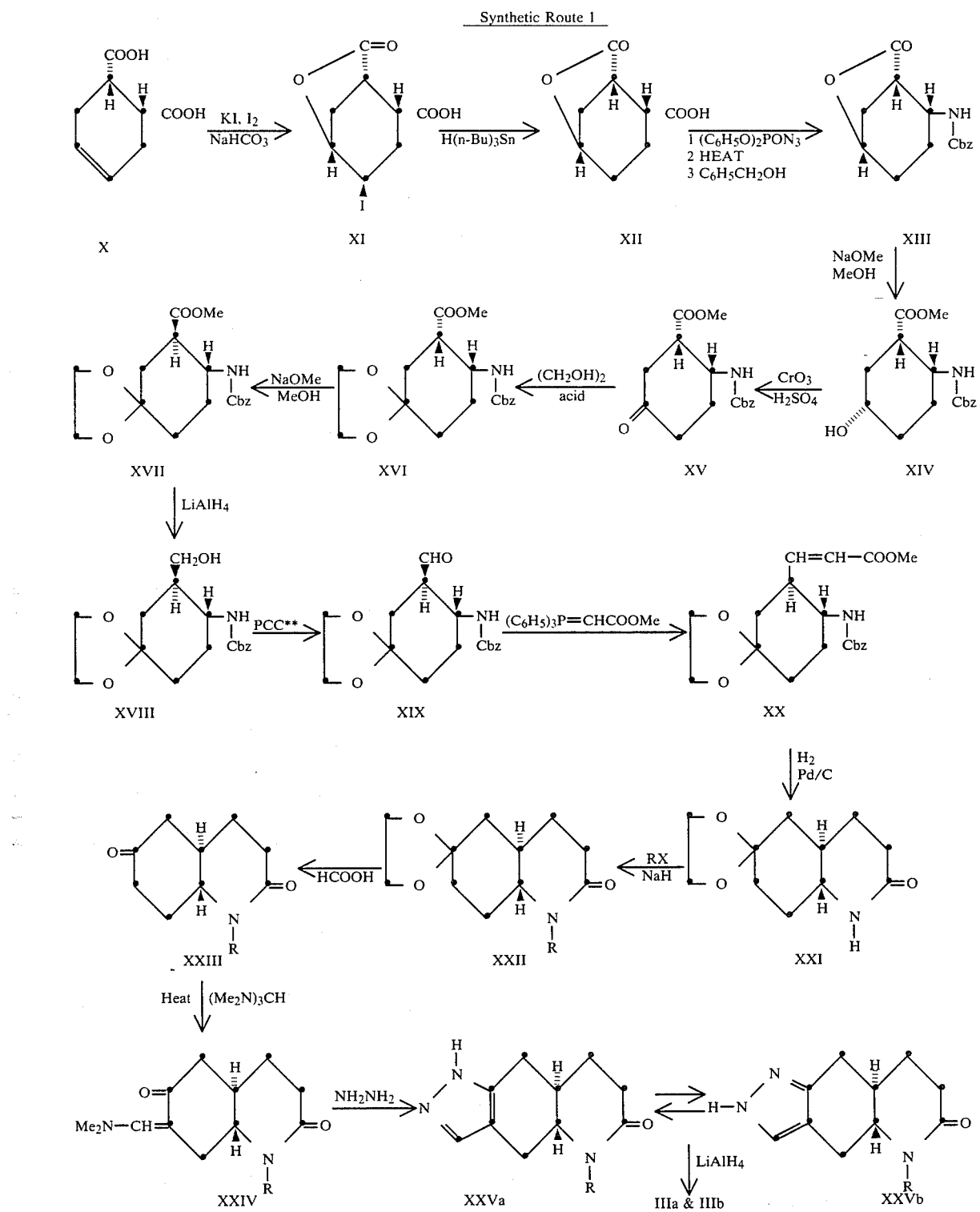

Synthetic Route 1 wherein R is H, $C_{1-3}$ straight-chain alkyl or allyl; *Cbz is CO—O-benzyl; **PCC is pyridinium chlorochromate.

In the above formulas, XIII thru XX, an amine protecting group, Cbz or benzyloxycarbonyl, is illustrated but it will be apparent that other protecting groups of the formula CO—W, wherein W is $OC_{1-3}$ alkyl or O-phenyl $C_{1-2}$ alkyl could be used.

In the above Synthetic Route I, cis-1,2,3,6-tetrahydrophthalic acid (X) is reacted with iodine and KI in sodium bicarbonate solution to yield cis-(±)-5-iodoperhydrophthalic acid 2,4-cyclolactone (XI). Treatment of this derivative with tri-n-butyltin hydride removes the iodo group (XII). Next, a Curtius Rearrangement is carried out on the free carboxylic acid group at C-1 in XII with DDPA (diphenylphosphorylazide). After heating the reaction mixture, benzyl alcohol is added to produce a cis-(±)-6-benzyloxycarbonylaminoperhydrobenzoic acid, 1,3-cyclolactone (XIII). The lactone ring is then opened with base, preferably sodium methylate in methanol, to form methyl cis-(±)-6-benzyloxycarbonylamino-3-hydroxycyclohexanecarboxylate (XIV). Oxidation of the secondary alcohol with Jones Reagent (chromic anhydride in dilute sulfuric acid) yields the corresponding 3-oxo derivative (XV). This ketone group is next protected by ketal formation as by reaction with ethyleneglycol in the presence of acid (XVI). This ketal is next isomerized with base, again preferably with sodium methylate in methanol to avoid transesterification problems, to give methyl trans-(±)-6-benzyloxycarbonylamino-3-ethyleneketalcyclohexylcarboxylate (XVII). The methyl ester group is next reduced to a primary alcohol (XVIII) with lithium aluminum hydride or other reducing agent with similar reducing capability. The primary alcohol is then oxidized to the corresponding aldehyde [XIX] using pyridinium chlorochromate which aldehyde is in turn reacted with the Wittig reagent, methyl(triphenylphosphoranylidene)acetate, to give methyl trans-(±)-3-(2-benzyloxycarbonylamino-5-ethyleneketal)acrylate (XX). Hydrogenation over a noble metal catalyst, conveniently 5% Pd/C, reduces the acrylate olefin and cleaves the carbobenzyloxy protecting group to give an intermediate which spontaneously cyclizes to trans-(±)-2,6-dioxo-6-ethyleneketaldecahydroquinoline (XXI). The ring nitrogen is alkylated or allylated to give a N—$C_{1-3}$ straight-chain alkyl or allyl derivative using conveniently an alkyl iodide or allyl halide and a suitable base such as sodium hydride. Next, the ketal protecting group is removed by acidic treatment, and the resulting trans-(±)-2,6-dioxo-1-substituted-decahydroquinoline reacted with tris-dimethylaminomethane to form the 7-dimethylaminomethylene derivative-(XXIV). Following the Kornfeld-Bach procedure, reaction with hydrazine produces trans-(±)-5-$C_{1-3}$ straight-chain alkyl or allyl-6-oxo-4,4a,5,6,7,8,8a,9-octahydro-1H(and 2H)pyrazolo[3,4-g]quinoline (XXVa and XXVb). Reduction of the lactam with lithium aluminum hydride or the like reducing agent yields trans-(±)-5-$C_{1-3}$ straight-chain alkyl or allyl-4,4a,5,6,7,8,8a,9-octahydro-1H(and 2H)-pyrazolo[3,4-g]quinoline (IIIa and IIIb).

The corresponding tautomeric pair when R is H can be prepared from XXI by eliminating the alkylation and carrying out the remaining procedure—removal of the ketal protecting group with acid, reaction with tris dimethylaminomethane at C-7, ring closure with hydrazine followed by LiAlH$_4$ reduction of the lactam carbonyl to yield ultimately trans-(±)-4,4a,5,6,7,8,8a,9-octahydro-1H(and 2H)-pyrazolo[3,4-g]quinoline, IIIa and IIIb when R is H. This tautomeric pair can be transformed to tautomers bearing a quinoline ring nitrogen substituent; ie., R=methyl, ethyl, n-propyl or allyl, by standard alkylation procedures using a base and an alkyl or allyl halide, care being taken to avoid such stringent reaction conditions that the pyrazole ring is also alkylated.

The above procedure yields a trans-(±)-racemate, which can be resolved by the method disclosed in the copending application of Titus and Kornfeld Ser. No. 439,238, filed Nov. 3, 1982 to yield the 4aR,8aR and 4aS,8aS tautomeric pairs. However, the dioxo derivative, XVa and XVb, or the corresponding compound wherein R is H, can also be resolved into its enantiomeric tautomers, 4aR,8aR-6-oxo-4,4a,5,6,7,8,8a,9-octahydro-1H(and 2H)-pyrazolo[3,4-g]quinolines and the corresponding 4aS,8aS tautomers.

Likewise, the bicyclic trans-(±)-2,6-dioxo derivatives XXIII can also be resolved into its enantiomers, 4aR,8aR-2,6-dioxo-5-$C_{1-3}$ straight-chain alkyl or allyldecahydroquinoline and the corresponding 4aS,8aS derivative.

Each enantiomer can then undergo separately the reactions XXIII→XXIV→XXVa+XXVb→IIIa+IIIb; ie., transformation to the 6-oxo-octahydro-pyrazoloquinoline and removal of the oxo group by LiAlH$_4$ reduction to yield where R is n-propyl 4aR,8aR-5-n-propyl-4,4a,5,6,7,8,8a,9-octahydro-1H(and 2H)-pyrazolo[3,4-g]quinoline or the corresponding 4aS,8aS enantiomer, depending on which enantiomeric 6-oxodecahydroquinoline is used. Thus, this invention provides the racemates XXVa⇌XXVb as well as a procedure for preparing both racemates and individual enantiomers.

4aR,8aR-5-n-propyl-6-oxo-4,4a,5,6,7,8,8a,9-octahydro-1H(and 2H)-pyrazolo[3,4-g]quinoline and 4aR,8aR-6-oxo-4,4a,5,6,7,8,8a,9-1H(and 2H)-pyrazolo[3,4-g]quinoline are disclosed and claimed in the copending application of Galick-Whitaker Ser. No. 637,354, filed this even date. The compounds are mammalian metabolic products of quinpirole and are optically active. There is no procedure known to racemize either of these derivatives; thus Galick-Whitaker (loc.cit.) does not provide the racemates nor any operative procedure for obtaining them, despite the fact that a racemate is implicitly disclosed by a disclosure of either enantiomer.

In Synthetic Route 1, X is a meso form and not optically active since it has a plane of symmetry. XI since it does not have a plane of symmetry is optically-active; is a cis-(±) or racemic form. However, in XI and all succeeding formulas thru XIX, only one of the cis or trans (as the case may be) enantiomers is pictured in order to simplify the reaction scheme, but a racemate is actually involved. In the bicycles XXI, XXII, XXIII, XXIV, XXVa⇌XXVb and IIIa⇌IIIb, no orientations are given but only the trans-(±) forms are prepared and thus only these forms are indicated by the structural formulas.

Specific Embodiment of the Invention

EXAMPLE 1

Preparation of Cis-(±)-5-iodoperhydrophthalic acid, 2,4-cyclolactone

A solution was prepared by dissolving 17.0 g. of cis-1,2,3,6-tetrahydrophthalic acid in 100 ml. of 10% aqueous sodium bicarbonate. An aqueous solotion of KI and I$_2$ was added thereto. The two solutions were thoroughly mixed and then allowed to stand at ambient temperature for 16 hrs. The reaction mixture was then shaken with saturated aqueous sodium thiosulfate to destroy excess iodine, as shown by the disappearance of a dark-brown color. The alkaline aqueous mixture was extracted with ether, and the ether extract separated and dried. Evaporation of the ether gave a pink residue weighing 22.3 g. The residue was treated with hot ethyl acetate, and the resulting mixture filtered. The filtrate was diluted with two volumes of hexane. Fine white needles of cis-(±)-5-iodoperhydrophthalic acid, 2,4-cyclolactone precipitated and were collected by filtration; M.P.=161°–164° C. The yield was 61%.

Analysis; Calc.; C, 32.46; H, 3.06; I, 42.86; Found; C, 32.19; H, 2.89; I, 42.68.

Infrared spectrum; 3190, 1763, 1724 cm$^1$

Ultraviolet spectrum; maxima at 207 ($\epsilon=330$), 259 ($\epsilon=620$).

EXAMPLE 2

Preparation of Cis-($\pm$)-perhydrophthalic acid, 2,4-cyclolactone

A solution was prepared by dissolving 60 g. of cis-($\pm$)-5-iodoperhydrophthalic acid, 2,4-cyclolactone in 200 ml. of 1,2-dimethoxyethane. To this solution was added 70.8 g. of tri-n-butyltinhydride. The reaction mixture was kept at room temperature for 3 days and was then poured into 10% aqueous sodium bicarbonate. The aqueous mixture was extracted thoroughly with ether, and the ether extract itself extracted with 10% aqueous sodium bicarbonate. The bicarbonate solutions were combined and then acidified with hydrochloric acid. The now-acidic layer was extracted with a 1:3 isopropanol/chloroform solvent mixture. The organic extract was evaporated to dryness to give a solid yellow residue weighing 34.1 g. Recrystallization of the solid from ethyl acetate/hexane gave 18.6 g of 1st crop and 10.4 g. of 2nd crop white crystalline cis-($\pm$)-perhydrophthalic acid, 2,4-cyclolactone.

EXAMPLE 3

Preparation of Cis-($\pm$)-2-benzyloxycarbonylaminocyclohexanecarboxylic acid, 1,3-cyclolactone A solution was prepared by dissolving 18.6 g. of cis-($\pm$)-perhydrophthalic acid, 2,4-cyclolactone in 235 ml. of THF. 12.1 g. of triethyl amine were added thereto. Next, a solution of 31.6 g. of diphenylphosphoryl azide in 50 ml. of THF was added in dropwise fashion at room temperature. The reaction mixture was warmed at about 30° C. for 20 min. and then at reflux temperature for about 3 hrs. The reaction mixture was then cooled to room temperature and stirred at that temperature overnight. 12.4 ml. of benzyl alcohol were added. This reaction mixture was heated to reflux for three hours and was then poured into water. The aqueous mixture was extracted with methylene dichloride. (The pH of the aqueous layer was about 7). The organic extract was dried, and the volatile constituents removed to leave a colorless oil weighing 50.6 g. The residual oil was dissolved in ether, and the ethereal solution chromatographed over silica. Initial fractions were shown to be unreacted benzyl alcohol. The next material to be eluted was cis-($\pm$)-2-benzyloxycarbonylaminocyclohexanecarboxylic acid, 1,3-cyclolactone. 9.5 g. of a white solid product were obtained.

EXAMPLE 4

Preparation of Methyl Cis-($\pm$)-2-benzyloxycarbonylamino-5-hydroxycyclohexanecarboxylate A solution was prepared by dissolving 1.19 g. of Na in 250 ml. of MeOH. A second solution of 14.2 g. of the cyclolactone from Example 3 in 50 ml. of MeOH and 25 ml. of methylene dichloride was added. After solution was complete, the mixture was poured into dilute aqueous sodium bicarbonate, and the new mixture acidified with dilute hydrochloric acid. The acidic aqueous mixture was extracted with methylene dichloride and the extract dried. Evaporation of the solvent yielded 15.9 g. of a colorless oil comprising methyl cis-($\pm$)-2-benzyloxycarbonylamino-5-hydroxycyclohexanecarboxylate; yield=about 100%. NMR was consistent with the proposed structure.

EXAMPLE 5

Preparation of Methyl Cis-($\pm$)-2-benzyloxycarbonylamino-5-oxocyclohexanecarboxylate A solution was prepared by dissolving 15.8 g. of the alcohol from Example 4 in 400 ml. of acetone. The solution was cooled to about 0° C., and 12 ml. of Jones Reagent added thereto in dropwise fashion over a 30 min. period. TLC indicated complete oxidation of the secondary alcohol to give methyl cis-($\pm$)-2-benzyloxycarbonylamino-5-oxoperhydrobenzoate. The green solid which had formed was separated from the supernatant by decantation, and washed three times with acetone. The supernate and washes were neutralized with aqueous sodium bicarbonate. The neutralized solution was filtered thru CELITE, and the filtrate concentrated. The concentrate was poured into water, and the aqueous mixture extracted with methylene dichloride. The extract was separated and dried, and the solvent removed therefrom. About 15.9 g. of a lightly colored oil (100% yield) comprising methyl cis-($\pm$)-2-benzyloxycarbonylamino-5-oxocyclohexanecarboxylate were obtained. NMR was consistent with the postulated structure for the 5-oxo derivative.

EXAMPLE 6

Preparation of Methyl cis-($\pm$)-2-benzyloxycarbonylamino-5-ethyleneketalcyclohexylcarboxylate A reaction mixture, prepared from 51.5 millimoles of methyl cis-($\pm$)-2-benzyloxycarbonylamino-5-oxocyclohexylcarboxylate, 6.4 g. of ethylene glycol, 100 mg. of p-toluenesulfonic acid monohydrate and 250 ml. of benzene, was heated to reflux for about 3 hrs in an apparatus equipped with a Dean-Stark trap to collect water formed as a by-product of the reaction. After the theoretical amount of water had been collected the reaction mixture was allowed to come to room temperature where it was kept overnight. The reaction mixture was the poured into dilute aqueous sodium bicarbonate, and the bicarbonate layer extracted first with ether and then with methylene dichloride. The extracts were combined and dried. Evaporation of the solvents gave a residue comprising the desired ketal; weight=17.32 g. The ketal was purified by chromatography over silica using a 2:1 ether/hexane solvent mixture as the eluant. Early fractions gave 14.61 g. (81.5%) yield of a faintly pink oil comprising purified methyl cis-($\pm$)-2-benzyloxycarbonylamino-5-ethyleneketalcyclohexylcarboxylate.

EXAMPLE 7

Isomerization of Methyl Cis-($\pm$)-2-benzyloxycarbonylamino-5-ethyleneketalcyclohexanecarboxylate to the Corresponding Trans-($\pm$) Derivative A solution of sodium methylate in methanol was prepared by adding 960 mg. of sodium to 200 ml. of methanol. 14.5 g. of methyl cis-($\pm$)-2-benzyloxyamino-5-ethyleneketalperhydrobenzoate were added and the mixture refluxed for 2$\frac{3}{4}$ hrs. TLC indicated an equilibrium mixture of the cis and trans racemates. The reaction mixture was poured into dilute hydrochloric acid, and the acidic mixture extracted with methylene dichloride. The organic extract was separated and dried. Evaporation of the solvent gave a residual oil; weight=14.8 g. The oil was chromatographed over silica using 2:1 ether/hexane as the eluant. Early fractions were shown to be a 5:2 mixture of the trans and cis isomers. Later fractions were collected and shown by TLC to be nearly pure trans racemate; weight=8.4 g.

EXAMPLE 8

Preparation of Trans-(±)-2-benzyloxyamino-5-ethylene ketal cyclohexylcarbinol

A solution of 8.4 g. of methyl trans-(±)-2-benzyloxycarbonylamino-5-ethyleneketalcyclohexylcarboxylate in 75 ml. of ether was added to a solution of 910 mg. of LiAlH$_4$ in 225 ml. of ether. The reaction mixture was stirred at room temperature for about 10 min., at which time TLC showed no remaining starting material. The reaction was decomposed by the addition, in order, of 0.9 ml. of water, 0.9 ml. of 15% sodium hydroxide and 2.7 ml. of water. The decomposed reaction was filtered to remove inorganic salts. The organic layer was concentrated in vacuo. 4.47 g. of a yellow oil were obtained. Chromatography of the oil over silica using ether as the eluant gave 2.39 (31%) of a colorless oil comprising purified trans-(±)-2-benzyloxycarbonylamino-5-ethyleneketalcyclohexylcarbinol.

EXAMPLE 9

Preparation of Trans-(±)-2-benzyloxycarbonylamino-5-ethyleneketalcyclohexylaldehyde A solution was prepared by dissolving 2.39 g. of the carbinol from Example 8 in 150 ml. of methylene dichloride. Ten grams of pyridinium chlorochromate were added, and the reaction mixture stirred vigorously at room temperature for about 2 hrs. An equal volume of ether was added. The resulting supernatant was separated and flash chromatographed over a silica column. The solid residue from the reaction was rinsed several times with ether and with methylene dichloride, and these rinses also passed through the flash silica column. Concentration of the eluate yielded a residue; total combined residue=about 2.1 g. (88% yield) of the desired trans-(±)-2-benzyloxycarbonylamino-5-ethyleneketalcyclohexylaldehyde.

EXAMPLE 10

Preparation of Trans-(±)-2,6-dioxodecahydroquinoline, 6-ethyleneketal

A reaction mixture was prepared by dissolving 1.6 g. of the aldehyde from the Example 9 and 2.5 g. of methyl(triphenylphosphoranylidene)acetate in 40 ml. of benzene. The reaction mixture was heated to reflux temperature for about 19 hrs. and was then concentrated in vacuo. The residue which showed no aldehyde by TLC, was chromatographed over silica using ether as the eluant. The first product to come off the column was the desired acrylic acid ester, which was a colorless oil; weight=1.3 g. (70% yield).

A solution was prepared by dissolving 1.30 g. of the above acrylic acid ester in 100 ml. of MeOH. 135 mg. of 5% Pd/C were added, and the mixture hydrogenated by vigourous slurrying under a hydrogen atmosphere. After one-half hour, an additional 250 mg. of catalyst were added, and the mixture slurried for an additional hour under hydrogen. TLC at this point showed no starting material present. The catalyst was separated by filtration, and the filtrate concentrated to give a cloudy oil which solidified on standing. TLC showed a mixture of the decahydroquinoline cyclized product and the uncyclized compound, methyl trans-(±)-3-(2-amino-5-ethyleneketalcyclohexyl)propionate. The product was dissolved in 200 ml. of THF, and the solution heated to reflux temperature for 2 hrs. The solvent was evaporated in vacuo, and the residue chromatographed over silica using THF as the eluant. Fractions 6–13 yeilded 429 mg. of a white solid comprising purified trans-(±)-2,6-dioxo-6-ethyleneketaldecahydroquinoline.

EXAMPLE 11

Preparation of Trans-(±)-2,6-dioxodecahydroquinoline

A solution prepared by dissolving 40 mg. of the ketal from Example 10 in 5 ml. of formic acid, was stirred at room temperature for about 30 min. At this time, TLC indicated that the de-ketalization had gone substantially to completion. The reaction mixture was therefore concentrated in vacuo to give 35 mg. of a white solid. The solid was chromatographed over silica using 1:19 MeOH/CH$_2$Cl$_2$ as the initial eluant followed by 1:9 MeOH/CH$_2$Cl$_2$ eluant. Later fractions with the second eluant (fractions 6–15) yielded 33 mg. of trans-(±)-2,6-dioxodecahydroquinoline. The compound had the following physical characteristics: Mass spectrum: ions at 167, 111, 110, 97, 84 and 56. Infrared spectrum (CHCl$_3$): 3400, 1716, 1661 cm$^{-1}$.

EXAMPLE 12

Preparation of Trans-(±)-6-oxo-4,4a,5,6,7,8,8a,9-octahydro-1H(and 2H)-pyrazolo[3,4-g]quinoline A solution was prepared by dissolving 168 mg. of trans-(±)-2,6-dioxodecahydroquinoline in 10 ml. of warm toluene; 0.4 ml. of tris(dimethylamino)methane were added, and the reaction mixture heated to reflux for 2.5 hrs. (A white solid began to appear at 1.5 hrs.). The reaction mixture was cooled to room temperature and then filtered. 148 g. of trans-(±)-2,6-dioxo-7-dimethylaminomethylenedecahydroquinoline were collected.

Three milligrams of the above derivative were dissolved in 0.5 ml. of MeOH containing one drop of anhydrous hydrazine added. The reaction mixture was stirred at room temperature for about 2 hrs., and was then diluted with water. The aqueous phase was extracted with CH$_2$Cl$_2$ and the extract dried. Removal of the solvent gave 2 mg. of a white solid comprising trans-(±)-6-oxo-4,4a,5,6,7,8,8a,9-octahydro-1H(and 2H)-pyrazolo[3,4-]quinoline formed in the above reaction. NMR on the product was consistent with the proposed structure.

This compound can be reduced with LiAlH$_4$ to yield the tautomeric pair, trans-(±)-4,4a,5,6,7,8,8a,9-octahydro-1H(and 2H)-pyrazolo[3,4-g]quinoline, a useful intermediate to prepare dopamine D-2 agonists by alkylation or allylation of the quinoline ring nitrogen by standard procedures.

EXAMPLE 13

Preparation of
Trans-(±)-1-n-propyl-2,6-dioxodecahydroquinoline

A solution was prepared by dissolving 390 mg. of trans-(±)-2,6-dioxo-6-ethyleneketaldecahydroquinoline from Example 10 in 15 ml. of THF. This solution was added to a suspension of 150 mg. of sodium hydride in 5 ml. of THF. The reaction mixture was stirred at room temperature for 1 hr. at which time 2 ml. of DMF and 0.9 ml. of n-propyl iodide were added. This new reaction mixture was stirred at room temperature for 22 hrs. at which time TLC showed that the reaction had gone substantially to completion. The reaction mixture was poured into water and the aqueous mixture extracted with 1:3 isopropanol/chloroform. The extract was separated, and the solvents removed therefrom to give 575 mg. of a yellow oil. Chromatography of the oil over silica using 5:4 THF/pentane as the eluant gave the following results: early fractions (3–5) gave 461 mg. (86% yield) of trans-(±)-1-n-propyl-2,6-dioxo-6-ethyleneketaldecahydroquinoline. The ketal group was removed with formic acid by the procedure of Example 11 to yield trans-(±)-1-n-propyl-2,6-dioxodecahydroquinoline. A 91% yield of the dioxo derivative was obtained. The compound had the following physical characteristics: Mass spectrum: ions at 209, 180, 152, 139, 124, 110.

Substitution of methyl or ethyliodide or of allyl chloride for n-propyliodide in the above example yields, eventually, the corresponding trans-(±)-5-methyl, ethyl or allyl-2,6-dioxodecahydroquinoline.

EXAMPLE 14

Preparation of
Trans-(±)-5-n-propyl-6-oxo-4,4a,5,6,7,8,8a,9-octahydro-1H(and 2H)-pyrazolo[3,4-g]quinoline Following the procedure of Example 12, trans-(±)-1-n-propyl-2,6-dioxodecahydroquinoline was reacted with tris(dimethylamino)methane to yield the corresponding 7-dimethylaminomethylene derivative. This compound was in turn reacted with anhydrous hydrazine to give trans-(±)-5-n-propyl-6-oxo-4,4a,5,6,7,8,,8a,9-octahydro-1H(and 2H)-pyrazolo[3,4-g]quinoline in 70% overall yield. Trans-(±)-1-n-propyl-6-oxo-7-dimethylaminomethylenedecahydroquinoline had the following physical characteristics: Mass spectrum; ions at 264, 219, 152, 150, 125, 112, 110, 82. Infrared spectrum: 3465, 1624 cm$^{-1}$.

Reduction of the above 6-oxo derivative with LiAlH$_4$ yields trans-(±)-5-n-propyl-4,4a,5,6,7,8,8a,9-octahydro-1H(and 2H)-pyrazole[3,4-g]quinoline.

While the above synthetic procedure has culminated in the production of trans-(±)-5-n-propyl-6-oxo-4,4a,5,6,7,8,8a,9-octahydro-1H(and 2H)-pyrazolo[3,4-g]quinoline, the intermediate trans-(±)-1-n-propyl(or methyl, ethyl or allyl)-2,6-dioxodecahydroquinoline from Example 13 or the corresponding 1-unsubstituted derivative from Example 11 can be reacted with bromine to yield a 7-bromo derivative and that intermediate reacted with an isothiourea of the formula $$\underset{HS-C-NR^1R^2}{\overset{NH}{\parallel}}$$

wherein each of R$^1$ and R$^2$ is individually methyl, ethyl or n-propyl.

The product of this reaction is a racemic trans-(±)-7-amino(NR$^1$R$^2$)-6-permissibly substituted-6-oxo-4,4a,5,6,7,8,8a,9-octahydro thiazolo[4,5-g]quinoline, composed of the enantiomers XXXa and XXXb below or with an enantiomeric starting material to yield either XXXa or XXXb.

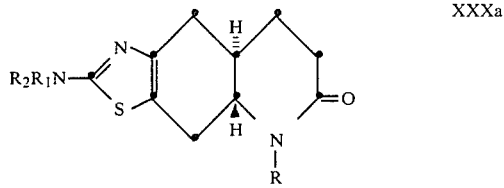

XXXa

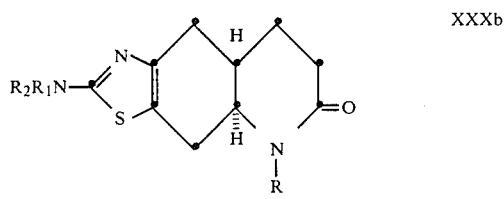

XXXb wherein R$^1$ and R$^2$ have their previous meaning and R is H, methyl, ethyl, n-propyl or allyl.

The 6-oxo group can then be reduced with LiAlH$_4$ to yield the racemic or enantiomeric dopamine D-2 agonist disclosed in Titus and Kornfeld, Ser. No. 604,687, filed 4-27-84 the trans-(±)-2-amino-5-permissibly substituted octahydrothiazolo[4,5-g]quinoline XXXIa (4aR,8aR) and XXXIb (4aS,8aS).

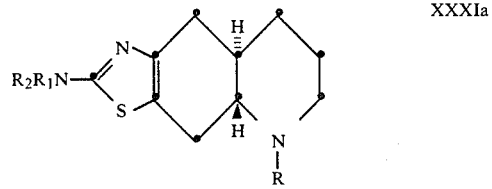

XXXIa

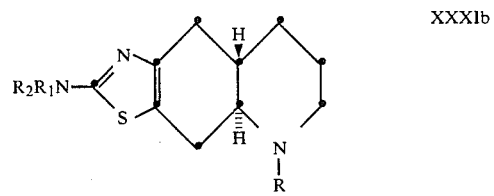

XXXIb

In XXXIa and XXXIb, if R is H, the quinoline nitrogen must be alkylated or allylated to give a dopamine agonist (D-1 or D-2). Since the cyclization to yield an thiazole ring is carried out on a 6-bromo-5-oxodecahydroquinoline, and since bromination might also react with the double bond of a 1-allyl derivative, to prepare such allyl compounds, I prefer to brominate the trans-(±)-1-unsubstituted 2,6-dioxodecahydroquinoline, cyclize the bromo derivative with isothiourea to yield a 6-oxothiazolo[4,5-a]quinoline, remove the 6-oxo group with LiAlH$_4$ and then allylate at N-5 to give the N-allyl dopamine agonist of Titus and Kornfeld (loc. cit.). Alternatively, the order of the LiAlH$_4$ reduction and N-5 alkylation steps can be reversed.

Similarly, the reaction of a trans-(±)-1-permissibly-substituted-2,6-dioxo-7-bromodecahydroquinoline or a 4aR,8aR or a 4aS,8aS enantiomer thereof with an isourea of the formula

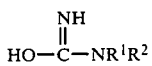

yields a racemic trans-(±)-2-amino-5-permissibly-substituted-6-oxo-4,4a,5,6,7,8,8a,9-octahydro[4,5-g]quinoline, structures XXXIIa (4aR,8aR) and XXXIIb (4aS,8aS) or the individual enantiomers thereof.

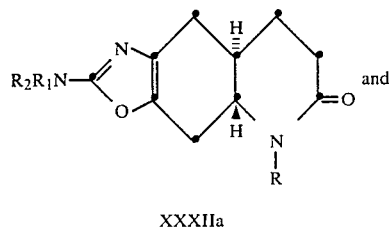

XXXIIa

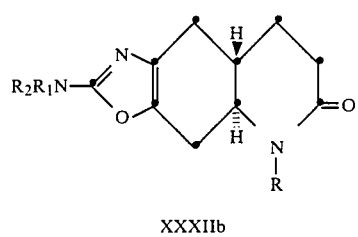

XXXIIb

Reduction of the racemate or either enantiomer with LiAlH₄ yields the 2-amino-5-substituted octahydrooxazolo[4,5-g]quinolines of Schaus and Titus Ser. No. 637,232, filed this even date, of structures XXXIIIa (4aR,8aR or XXXIIIb (4aS,8aS)

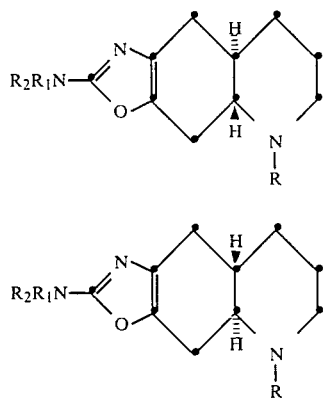

wherein R is H, $C_{1-3}$ straight-chain alkyl or allyl.

As with the thiazoles, preparation of a compound according to XXXIIIa or XXXIIIb where R is allyl, is better carried out by allylating a 2-amino-6-oxo-octahydro-oxazolo[4,5-g]quinoline (XXXIIa and XXXIIb) and then reducing the N-allyl lactam or by allylating the final oxazolo[4,5-g]quinoline (XXXIIIa and XXXIIIb when R is H).

Reaction of the racemate XXIV (from Synthetic Route 1) or an enantiomer thereof with guanidine or a substituted guanidine

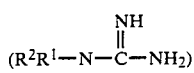

yields a 7-oxo-6-permissibly-substituted octahydropyrimido[4,5-g]quinoline of the formulas, XXXVa (5aR,9aR) and XXXVB (5aS,9aS)

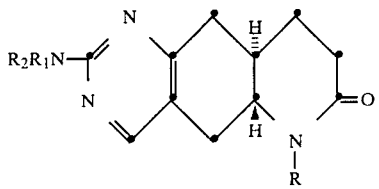
XXXVa

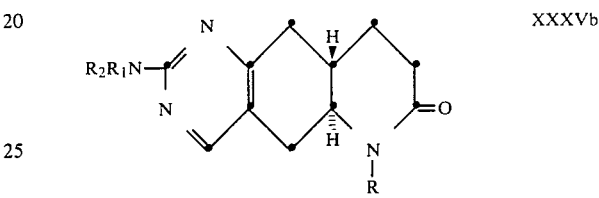
XXXVb where R is H, $C_{1-3}$ straight-chain alkyl or allyl and $R^1$ and $R^2$ have their previous meaning. Reduction of the lactam with LiAlH₄, optionally followed by alkylation or allylation where R is H, yields the powerful dopamine D-2 agonists, the racemate and the 5aR,9aR enantiomer, XXXVIa and the D-1 agonist, the enantiomer XXXVIb. (In the D-1 and D-2 agonists, R is not H).

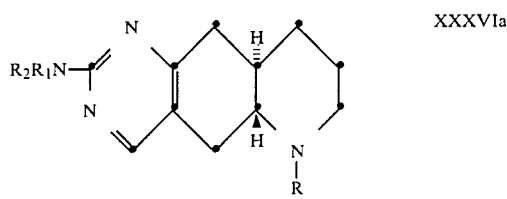
XXXVIa

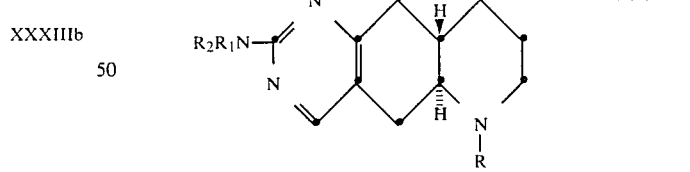
XXXVIb

While the procedure in Synthetic Route I produces only racemic materials, the individual enantiomers, the 6-oxo-octahydro-1H(and 2H)-pyrazolo[3,4-g]quinolines, IIIa and IIIb, the 6-oxo-octahydrothiazolo[4,5-g]quinolines, XXXa and XXXb, the 6-oxo-octahydro-oxozolo[4,5-g]quinolines, XXXIIa and XXXIIb, and the 7-oxo-octahydropyrimido[4,5-g]quinolines, XXXVa and XXXVc, can be prepared by resolution of the racemates. Alternatively, the trans-(+)-1-permissibly-substituted-2,6-dioxodecahydroquinoline, XXXVIIa (4aR,8aR) and XXXVIIb (4aS,8aS)

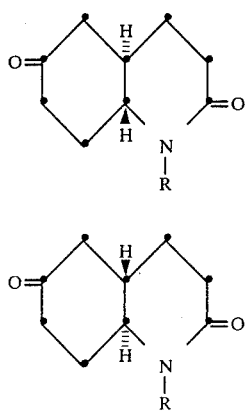

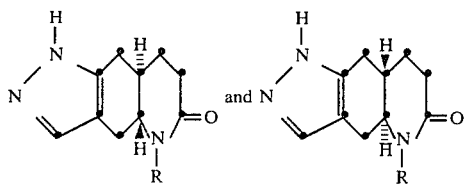

can be resolved by ketalization with (+)- or (−)-2,3-butanediol, chromatographic separation of the diastereomers followed by removal of the ketal to yield an optically-active ketone. The enantiomeric secondary amide (R=H is XXXVIIa or XXXVIIb) can then be alkylated or allylated and the resulting tertiary amine cyclized to a pyrazole, thiazole, oxazole, or pyrimidine containing a lactam group and the lactam reduced with LiAlH$_4$ to yield the D-2 or D-1 dopamine agaonist directly. Alternatively, the enantiomeric secondary amine (R=H) in XXXVIIa or in XXXVIIb can be annelated, the lactam reduced and the resulting compound allylated or alkylated to yield enantiomeric 4aR,-8aR or 5aR,9aR dopamine D-2 agonist or an entantomeric 4aS,8aS or 5aS,9aS dopamine D-1 agonist.

Alternatively, a carboxylic ester XIV, XV, XVI, XVII, or XX from Synthetic Route 1 can be hydrolyzed to the corresponding carboxylic acid and the acid treated with an optically active base to produce diastereomers which can be separated chromatographically or by crystallization. The optically-active esters can then readily be reconstituted by ester cleavage. Also, compound XVIII is an alcohol which can be esterified with an optically active acid, the resulting diastereomers separated and the optically active alcohol obtained by hydrolysis. Similarly, the protected α-amino esters XIV, XV, XVI, XVII and XVIII can be deprotected, the primary amine neutralized with an optically-active acid, the diastereoisomeric salts separated, the optically-active amine recovered from the salt and the amine group reprotected with the same or a different group.

Again, alternatively, the acids XI or XII can be neutralized by an optically-active amine and the salts separated by recrystallization. Acidification allows for the isolation of the optically-active acids. See *Angew. Chem. 2nd Ed.* English 23 (1), 67 (1984) for the preparation of cis-(±)-1,2,3,5-tetrahydrophthalic acid, monomethyl ester and separation of the enantiomeric half-acid esters to yield a >94% ee enantiomer.

I claim:

1. The trans-(±)-tautomers composed of the tautomeric enantiomers wherein R is H, allyl or C$_{1-3}$ straight-chain alkyl.

2. Trans-(+)-(4aS,8aS) tautomers according to claim 1.

3. Racemic tautomers according to claim 1 in which R is n-propyl.

4. The trans-(±)racemate composed of trans-(−) and trans-(+)enantiomers of the formula

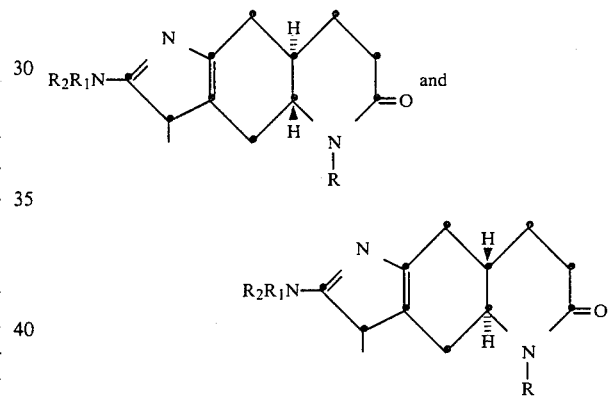

wherein R is H, allyl or C$_{1-3}$ straight-chain alkyl, R$^1$ and R$^2$ are individually H, methyl, ethyl or n-propyl, and Y is S or O.

5. A trans-(−)-(4aR,8aR)enantiomer according to claim 4.

6. A racemate according to claim 4 in which R is n-propyl.

7. A trans-(−)enantiomer according to claim 4 in which R is n-propyl.

8. A racemate according to claim 4 in which R$^1$ and R$^2$ are individually H or methyl.

9. A trans-(−)-(4aR,8aR)enantiomer according to claim 4 in which R$^1$ and R$^2$ are individually H or methyl.

10. A racemate according to claim 4 in which both R$^1$ and R$^2$ are H.

11. A trans-(−)-(4aR,8aR)enantiomer according to claim 4 which R$^1$ and R$^2$ are both H.

12. A racemate according to claim 4 in which Y is S.

13. A trans-(−)-(4aR,8aR)enantiomer according to claim 4 in which Y is S.

14. A racemate according to claim 4 in which Y is O.

15. A trans-(−)-(4aR,8aR)enantiomer according to claim 4 in which Y is O.

16. A trans-(±)racemate composed of enantiomers of the formulas

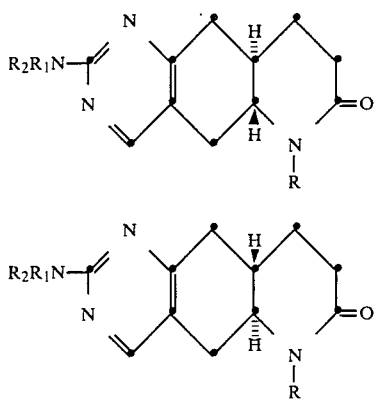

wherein R is H, allyl or $C_{1-3}$ straight-chain alkyl, and $R^1$ and $R^2$ are individually H or $C_{1-3}$ straight chain alkyl.

17. A racemate according to claim 16 in which R is n-propyl.

18. A racemate according to claim 16 in which $R^1$ and $R^2$ are individually H or methyl.

19. A racemate according to claim 18 in which $R^1$ and $R^2$ are both H.

20. A 5aR,9aR enantiomer according to claim 16 in which R is n-propyl.

21. A 5aR,9aR enantiomer according to claim 16 in which $R^1$ and $R^2$ are H or methyl.

22. A 5aR,9aR enantiomer according to claim 21 in which both $R^1$ and $R^2$ are H.

23. A trans-(±)racemate composed of enantiomers of the formula

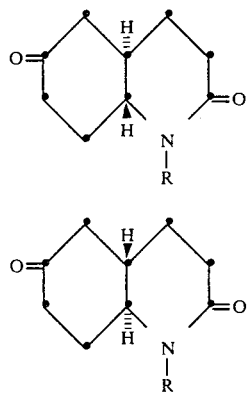

wherein R is H, allyl or $C_{1-3}$ straight-chain alkyl.

24. A trans-(±)racemate composed of enantiomers of the formula

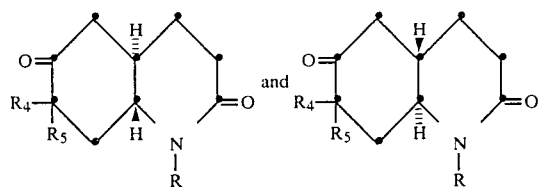

wherein R is H, allyl or $C_{1-3}$ straight-chain alkyl, and, when taken singly, one of $R^4$ and $R^5$ is H and the other Br or formyl and when taken together, $R^4$ and $R^5$ represent dimethylaminomethylene.

25. A trans-(−)enantiomer of the racemate of claim 24.

26. Compounds of the formulas

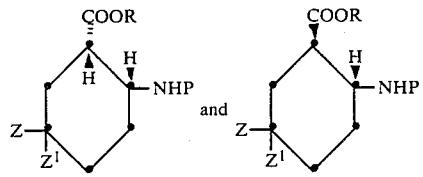

wherein R is $C_{1-3}$alkyl or H, Z and $Z^1$ with the carbon to which they are attached represent a carbonyl or an ethylene ketal, P is H, $C_{1-3}$alkyl or a protecting group, CO—W, wherein W is phenyl $C_{1-2}$alkyloxy, $C_{1-3}$alkyloxy, H or $C_{1-3}$alkyl.

27. The process which comprises hydrogenating over a nobel metal catalyst a trans racemate of the formula

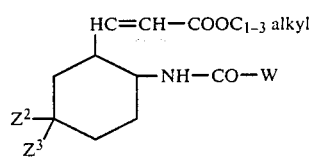

wherein W is O—$C_{1-3}$alkyl or —O—$C_{1-2}$alkylphenyl, $Z^2$ and $Z^3$ are, individually, $C_{1-2}$alkyloxy and, taken together, O—$(CH_2)_2$—O to yield a trans racemate of the formula

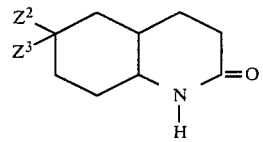

alkylating or allylating said cyclic lactam with a straight chain $C_{1-3}$alkyl halide or allyl halide in the presence of a base to yield a trans racemate of the formula

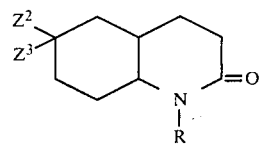

wherein R is $C_{1-3}$ straight chain alkyl or allyl and $Z^2$ and $Z^3$ have their previous meaning, treatment of which with acid in a mutual solvent, yields a trans racemate of the formula

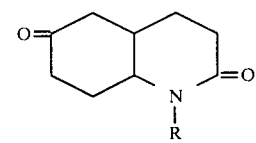

wherein R has its previous meaning and then, optionally, reacting said compound with tridimethylaminomethane to yield a trans racemate of the formula

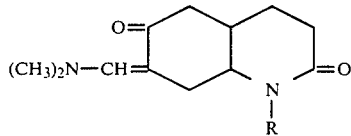

wherein R has its previous meaning.

28. The process which comprises hydrogenating over a noble metal catalyst a trans racemate of the formula

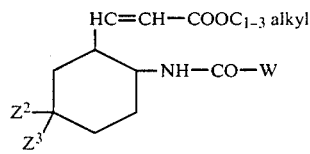

wherein W is O—$C_{1\text{-}3}$alkyl or —O—$C_{1\text{-}2}$alkylphenyl, $Z^2$ and $Z^3$ are, individually, $C_{1\text{-}2}$alkyloxy and, taken together, O—$(CH_2)_2$—O to yield a trans racemate of the formula

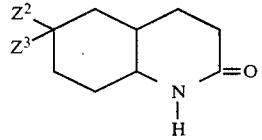

treatment of which with acid in a mutual solvent yields a trans racemate of the formula

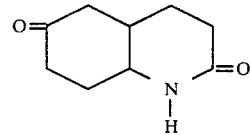

and then, optionally, reacting said compound with tridimethylaminomethane to yield a trans racemate of the formula

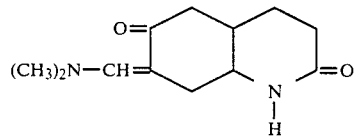

29. The process step which comprises simultaneously hydrogenating, deprotecting and cyclizing a trans racemate of the formula

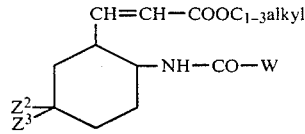

wherein W is O—$C_{1\text{-}3}$alkyl or O—$C_{1\text{-}2}$alkylphenyl and $Z^2$ and $Z^3$, taken individually are $C_{1\text{-}2}$alkyl and taken together O—$(CH_2)_2$—O, to yield a trans racemate of the formula

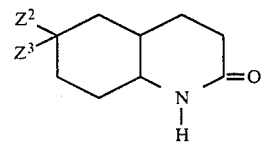

wherein $Z^2$ and $Z^3$ have their previous meaning.

* * * * *